United States Patent [19]  [11] 4,240,973
Linhart et al.  [45] Dec. 23, 1980

[54] N-CYCLOHEXYL-N-METHOX-YACETOACETAMIDE

[75] Inventors: Friedrich Linhart, Heidelberg; Bjoern Girgensohn, Mannheim; Bernd Zeeh, Ludwigshafen, all of Fed. Rep. of Germany

[73] Assignee: BASF Aktiengesellschaft, Fed. Rep. of Germany

[21] Appl. No.: 59,775

[22] Filed: Jul. 23, 1979

[30] Foreign Application Priority Data

Jul. 21, 1978 [DE] Fed. Rep. of Germany ....... 2832102

[51] Int. Cl.$^3$ ............................................... C07C 83/10
[52] U.S. Cl. ......................... 260/453 RW; 260/347.3
[58] Field of Search .................................. 260/453 RW

[56] References Cited

U.S. PATENT DOCUMENTS

| | | | |
|---|---|---|---|
| 3,691,234 | 9/1972 | Kiefer et al. | 260/453 RW X |
| 3,993,772 | 11/1976 | Pommer et al. | 424/285 |
| 4,013,684 | 3/1977 | Meckle et al. | 260/347.3 |

OTHER PUBLICATIONS

Houben–Weyl, Methoden der Organischen Chemie, vol. 7/4 (1968), pp. 234–236.

*Primary Examiner*—Richard Raymond
*Attorney, Agent, or Firm*—Keil & Witherspoon

[57] ABSTRACT

N-Cyclohexyl-N-methoxyacetoacetamide, its preparation and its use as an intermediate for the preparation of O-methyl-N-cyclohexyl-2,5-dimethylfuran-3-hydroxamic acid.

1 Claim, No Drawings

N-CYCLOHEXYL-N-METHOXYACETOACETAMIDE

The present invention relates to N-cyclohexyl-N-methoxyacetoacetamide, a process for its preparation, and its use as an intermediate for the preparation of O-methyl-N-cyclohexyl-2,5-dimethylfuran-3-hydroxamic acid.

Furan derviatives may be prepared by several methods familar to those skilled in the art. For example, the preparation of O-methyl-N-cyclohexyl-2,5-dimethylfuran-3-hydroxamic acid from 2,5-dimethylfuran-3-carboxylic acid chloride by reacting the latter with N-cyclohexylhydroxylamine and subsequently methylating the resulting intermediate with dimethyl sulfate has been disclosed (German Laid-Open Application DOS No. 2,455,082). However, this method is expensive and not entirely satisfactory, especially because 2,5-dimethylfuran-3-carboxylic acid chloride is difficult to prepare, and because by-products are formed.

We have found a process which is particularly suitable for the preparation of O-methyl-N-cyclohexyl-2,5-dimethylfuran-3-hydroxamic acid, an important fungicide. The starting material for the novel process of preparation is N-cyclohexyl-N-methoxyacetoacetamide. The latter is condensed with an α-acyloxypropionaldehyde in the presence of an acid catalyst, in accordance with the following equation:

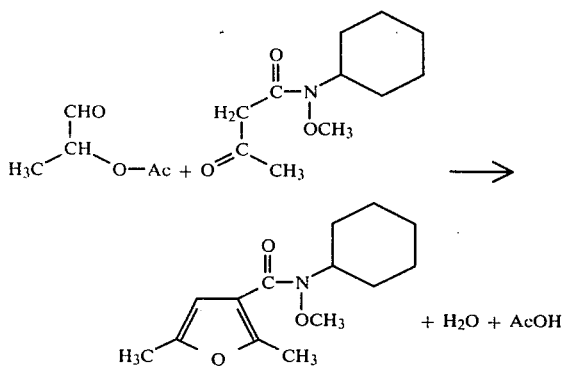

N-Cyclohexyl-N-methoxyacetoacetamide is a novel compound. The present invention is concerned with this compound, with its preparation and with its use for the synthesis of the furan derivative mentioned. The compound is obtained without difficulty by reacting O-methyl-N-cyclohexylhydroxylamine with diketene in the presence or absence of a solvent or diluent at from 0° to 80° C., preferably from 30° to 50° C. Suitable solvents or diluents are those which are inert under the reaction conditions, for example hydrocarbons and chlorohydrocarbons, eg. cyclohexane, gasolines, toluene, xylenes, chlorobenzenes and higher aromatics, ethers, eg. tetrahydrofurann and dioxane, esters, eg. ethyl acetate, amides, eg. dimethylformamide, chlorinated carbons and others, and mixtures of these liquids. However, it is also possible to use liquids which react more slowly with diketene than does O-methyl-N-cyclohexylamine, for example water. It is also possible to use the reaction product as a solvent and diluent.

Advantageously, the two components are reacted in the equimolar ratio, since the reaction virtually goes to completion and hence it is not necessary to recover one of the reactants, used in excess, from the reaction batch.

O-Methyl-N-cyclohexylhydroxylamine, used for the preparation of N-cyclohexyl-N-methoxyacetoacetamide, is known in the form of its hydrochloride (K. G. TAYLOR, S. R. ISAAC and M. S. CLARK, J. org. Chem. 41 (1976), 1135–40) and can easily be liberated from the latter by means of a base.

N-Cyclohexyl-N-methoxyacetoacetamide is used for the preparation of O-methyl-N-cyclohexyl-2,5-dimethylfuran-3-hydroxamic acid by reacting it with α-acetoxypropionaldehyde in a solvent which is inert under the reaction conditions, at from 20° to 80° C., preferably from 40° to 55° C. It is essential that the water formed in the reaction is removed from the reaction mixture, either by azeotropic distillation with a solvent, for example methylene chloride, or by (chemically) binding it with a drying agent, for example calcium chloride, magnesium sulfate, calcium sulfate, silica gel or molecular sieves or, advantageously, by means of the catalyst, for example iron-III chloride. In the last-mentioned case, substantial amounts of catalyst have to be employed. After decomposing the reaction mixture with water and separating off the organic phase and, where appropriate, removing the solvent, O-methyl-N-cyclohexyl-2,5-dimethylfuran-3-hydroxamic acid is obtained in very good yield and satisfactory purity. This result was not to be expected, according to German Laid-Open Application DOS No. 2,227,547, since the process disclosed there employs acetoacetamides which expressly do not carry any O-linked substituents on the amide nitrogen.

Examples of inert solvents in which the reaction to give the heterocyclic compounds can be carried out are alcohols, eg. isobutanol, methanol, ethanol, propanol, isopropanol and higher alcohols, halohydrocarbons, eg. dichloromethane, esters, eg. ethyl acetate, ethers, eg. tetrahydrofuran, dioxane and methylglycol, aromatic compounds, eg. benzene, toluene and xylene and other compounds, eg. cyclohexane.

Suitable acid catalysts are proton acids and Lewis acids, eg. p-toluenesulfonic acid, sulfuric acid, phosphoric acid and polyphosphoric acids amongst the first category and, eg., iron-III chloride, zinc chloride, tin-IV chloride, boron trifluoride and aluminum chloride amongst the latter category.

The reaction can be carried out under atmospheric or superatmospheric pressure of up to about 700 atmospheres, and can, if desired, also be carried out in an inert gas atmosphere.

Preferred acyl radicals in the α-acyloxypropionaldehyde are those of 1 to 4 carbon atoms, eg. formyl, acetyl, propionyl and butyryl.

α-Acyloxypropionaldehydes are known and may be obtained in the conventional manner by hydroformylation of the corresponding vinyl ester.

The Examples which follow illustrate the invention. Parts are by weight.

EXAMPLE 1

N-Cyclohexyl-N-methoxyacetoacetamide 84 parts of diketene are added dropwise to a solution of 129 parts of O-methyl-N-cyclohexylhydroxylamine in 400 parts of cyclohexane at 35°–45° C. To complete the reaction, the mixture is then stirred for 45 minutes at 45° C. After stripping off the solvent under reduced pressure, 213 parts of N-cyclohexyl-N-methoxyacetoacetamide, boiling at 113°–117° C./0.3 mm Hg, are obtained.

EXAMPLE 2

O-Methyl-N-cyclohexyl-2,5-dimethylfuran-3-hydroxamic acid

A mixture of 85.2 parts of N-cyclohexyl-N-methoxyacetoacetamide and 58.2 parts of 95.7% pure α-acetoxypropionaldehyde is added dropwise to a suspension of 19.4 parts of iron-III chloride in 100 parts of isobutanol at 40°–45° C. The mixture is then kept at 45° C. for 7.5 hours. Water is added to the reaction mixture, the batch is extracted with methylene chloride and the extract is evaporated. 104 parts of crude product are obtained; this can be distilled at 138°–145° C./0.3 mm Hg, to give 88.5 parts of pure O-methyl-N-cyclohexyl-2,5-dimethylfuran-3-hydroxamic acid.

EXAMPLE 3

O-Methyl-N-cyclohexyl-2,5-dimethylfuran-3-hydroxamic acid

A mixture of 85.2 parts of N-cyclohexyl-N-methoxyacetoacetamide and 58.8 parts of 94.7% pure α-acetoxypropionaldehyde is added in the course of 20 minutes to 7.6 parts of p-toluenesulfonic acid in 320 parts of methylene chloride. Water is then removed in the course of 7.5 hours by refluxing the mixture and using a water separator. When the reaction solution has cooled, it is extracted by shaking 3 times with 100 parts of water at a time, and is dried and evaporated. On distilling the resulting 103.2 parts of crude product, 90.6 parts of pure O-methyl-N-cyclohexyl-2,5-dimethylfuran-3-hydroxamic acid are obtained.

We claim:
1. N-Cyclohexyl-N-methoxyacetoacetamide.

* * * * *